United States Patent [19]
Ream

[11] Patent Number: 5,827,313
[45] Date of Patent: Oct. 27, 1998

[54] DEVICE FOR CONTROLLED LONGITUDINAL MOVEMENT OF AN OPERATIVE ELEMENT WITHIN A CATHETER SHEATH AND METHOD

[75] Inventor: John H. Ream, San Jose, Calif.

[73] Assignee: Boston Scientific Corporation, Natick, Mass.

[21] Appl. No.: 722,325

[22] Filed: Sep. 27, 1996

[51] Int. Cl.⁶ ............................. A61B 17/32; A61B 8/00
[52] U.S. Cl. ..................... 606/171; 606/159; 606/180; 600/471
[58] Field of Search .................... 128/660.03, 662.06, 128/916; 606/159, 170, 180, 171; 600/471, 463

[56] References Cited

U.S. PATENT DOCUMENTS

| | | |
|---|---|---|
| 4,593,699 | 6/1986 | Poncy et al. . |
| 4,708,125 | 11/1987 | Miketi et al. . |
| 4,771,774 | 9/1988 | Simpson et al. . |
| 4,794,931 | 1/1989 | Yock . |
| 4,802,487 | 2/1989 | Martin et al. . |
| 4,841,977 | 6/1989 | Griffith et al. . |
| 4,917,097 | 4/1990 | Proudian et al. . |
| 5,000,185 | 3/1991 | Yock . |
| 5,019,189 | 5/1991 | Farr .......................................... 606/159 |
| 5,048,529 | 9/1991 | Blumenthal . |
| 5,105,819 | 4/1992 | Wollschläger et al. . |
| 5,107,844 | 4/1992 | Kami et al. . |
| 5,125,410 | 6/1992 | Misono et al. . |
| 5,178,148 | 1/1993 | Lecoste et al. . |
| 5,203,338 | 4/1993 | Jang . |
| 5,211,176 | 5/1993 | Ishiguro et al. . |
| 5,318,576 | 6/1994 | Plassche, Jr. et al. . |
| 5,321,501 | 6/1994 | Swanson et al. . |
| 5,360,432 | 11/1994 | Shturman ............................. 606/170 X |
| 5,366,464 | 11/1994 | Belknap . |
| 5,373,849 | 12/1994 | Maroney et al. . |
| 5,383,460 | 1/1995 | Jang et al. ........................... 606/159 X |
| 5,398,690 | 3/1995 | Batten et al. .................. 128/662.06 X |
| 5,485,846 | 1/1996 | Webler et al. . |
| 5,490,859 | 2/1996 | Mische et al. ........................... 606/159 |
| 5,497,776 | 3/1996 | Yamakazi et al. . |
| 5,551,432 | 9/1996 | Iezzi . |
| 5,592,942 | 1/1997 | Webler et al. .................. 128/662.06 X |

FOREIGN PATENT DOCUMENTS

| | | |
|---|---|---|
| 0244058 | 11/1987 | European Pat. Off. . |
| 0266858 | 5/1988 | European Pat. Off. . |
| 0626152 | 11/1994 | European Pat. Off. . |

(List continued on next page.)

OTHER PUBLICATIONS

Brochure: ClearView Ultra™ System / UltraCross™ Catheters (in existence at least as of Sep. 26, 1996).

Jerome H. Siegel, MD, *Endoscopic Retrograde Cholangiopancreatography, Technique, Diagnosis, and Therapy*, pp. 5 and 400, Raven Press, New York.

Joseph E. Geenen, MD et al., *Techniques in Therapeutic Endoscopy*, Second Edition, pp. 1.14, 3.6, 7.4, 8.20, and 10.7, Gower Medical Publishing, New York:London.

*Primary Examiner*—Francis J. Jaworski
*Attorney, Agent, or Firm*—Townsend and Townsend and Crew LLP

[57] ABSTRACT

An operative element mover (22) is used as a part of an ultrasound imaging or other catheter system (2) including a hollow sheath (6) and a case (16) housing a rotary driver (10). A drive cable or other connecting member (8) is disposed within the sheath with a transducer (24) at its distal end (26) and its proximal end (12) coupled to the rotary driver. The rotary driver rotates the transducer about the longitudinal axis (14) of the sheath. A hemostasis valve (50) anchors the sheath to the patient where the sheath enters the patient. The transducer mover (22) is used to move the drive cable along the longitudinal axis and includes a body (38) fixedly mountable to and dismountable from the case and a movable anchor post (40). The anchor post is clipped to the sheath and is moved by a sheath anchor drive (46) to translate the sheath from or toward the case. This causes the transducer to move within the sheath in a proximal or distal longitudinal direction (52).

21 Claims, 10 Drawing Sheets

FOREIGN PATENT DOCUMENTS

| | | |
|---|---|---|
| 2543817 | 10/1984 | France . |
| 4344312 | 7/1994 | Germany . |
| 90/01300 | 2/1990 | WIPO . |
| 91/15154 | 10/1991 | WIPO . |
| 92/19930 | 11/1992 | WIPO . |
| 93/16642 | 9/1993 | WIPO . |
| 94/00052 | 1/1994 | WIPO . |
| WO 94/00052 | 1/1994 | WIPO . |
| 94/11038 | 5/1994 | WIPO . |
| 97/32182 | 9/1997 | WIPO . |

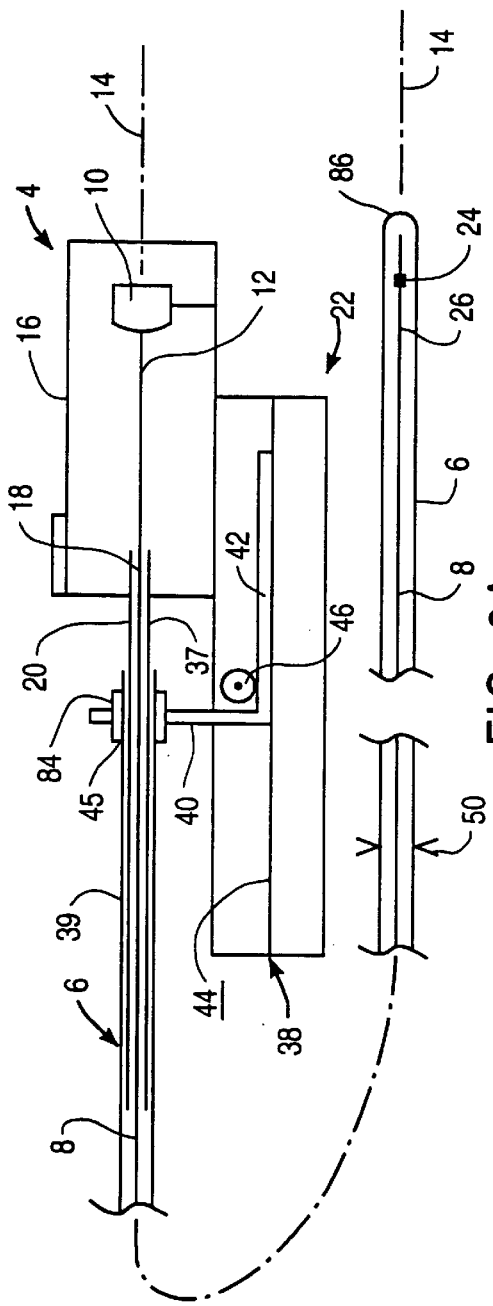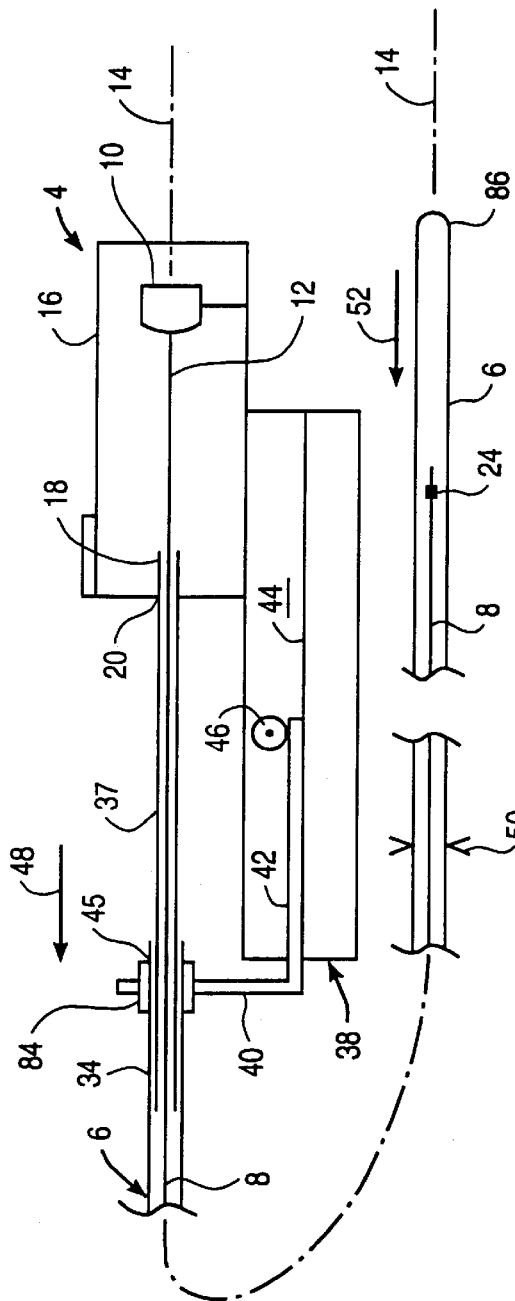

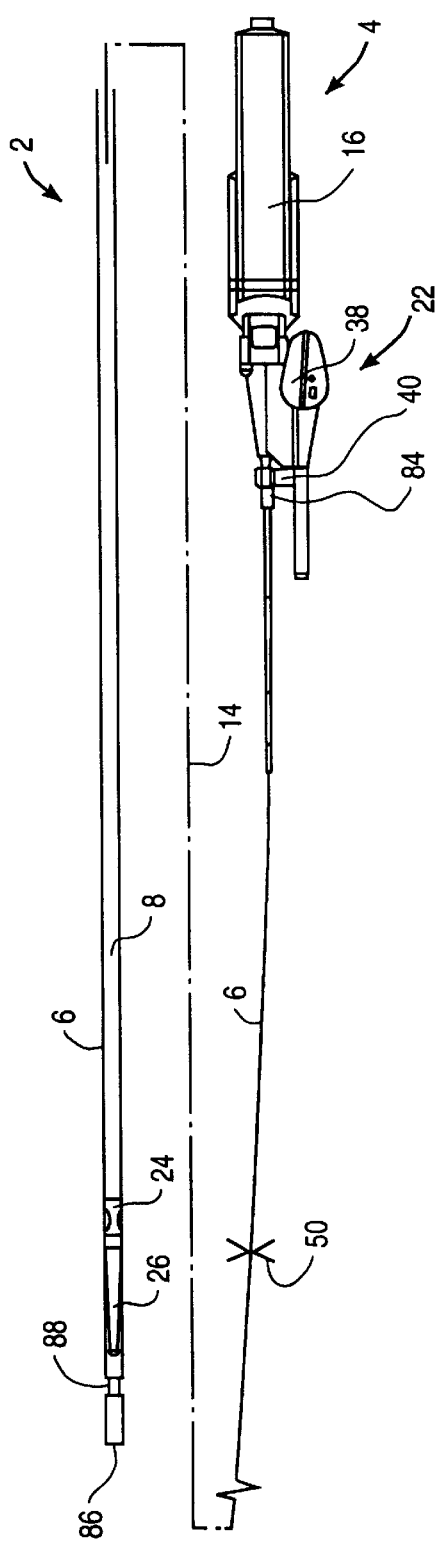
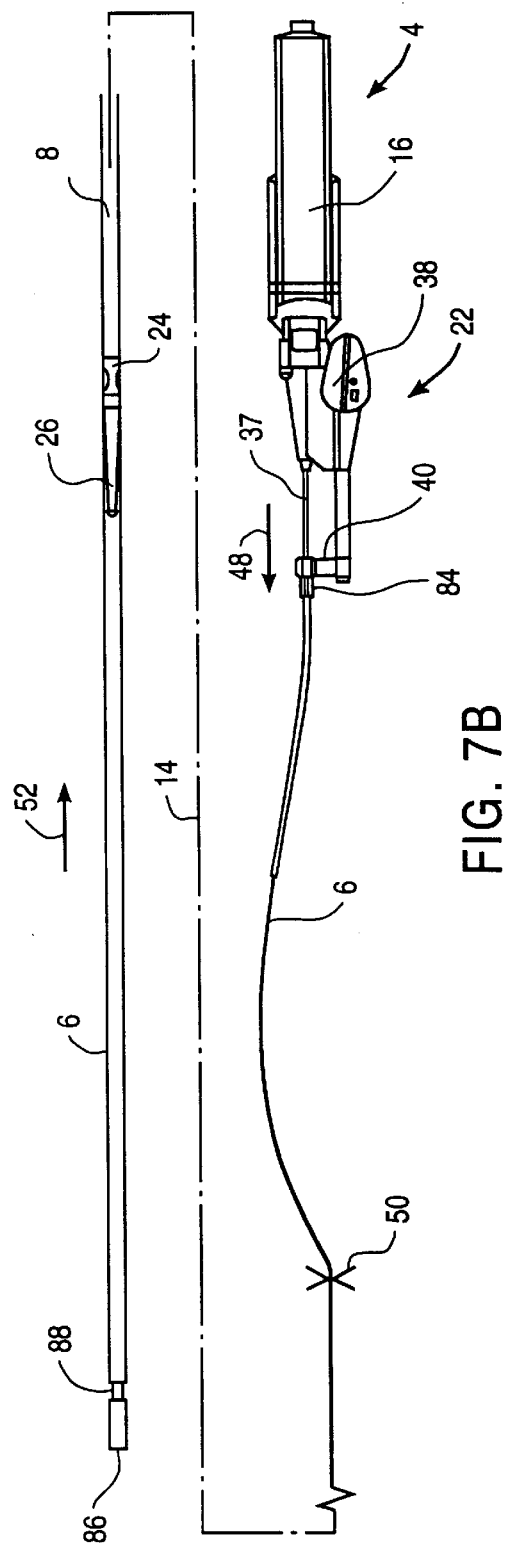
FIG. 7A
FIG. 7B

DEVICE FOR CONTROLLED LONGITUDINAL MOVEMENT OF AN OPERATIVE ELEMENT WITHIN A CATHETER SHEATH AND METHOD

BACKGROUND OF THE INVENTION

The present invention relates generally to catheter systems. More particularly, a longitudinal mover is provided which permits the controlled longitudinal movement of a catheter-transported operative device, such as a rotatable ultrasonic transducer, an optical fiber, or an atherectomy cutter, within a patient.

Arteriosclerosis, also known as atherosclerosis, is a common human ailment arising from the deposition of fatty-like substances, referred to as atheromas or plaque, on the walls of blood vessels. Such deposits occur in both peripheral blood vessels which feed the limbs of the body and the coronary vessels which feed the heart. When the deposits accumulate in localized regions of a blood vessel, stenosis, or narrowing of the vascular channel, occurs. Blood flow is restricted and the person's health is at serious risk.

Numerous approaches for reducing and removing such vascular deposits have been proposed, including balloon angioplasty where a balloon-tipped catheter is used to dilate a region of atheroma, and other devices that are pushed or pulled along or through a deposit, such as atherectomy where a blade or cutting bit is used to sever and remove the atheroma, spark gap reduction in which an electrical spark burns through the plaque, laser angioplasty where laser energy is used to ablate at least a portion of the atheroma, and opening of vessels through the use of stents.

Two major difficulties in using such devices are maintaining a constant translational rate for the device and obtaining images of and information on the region of the blood vessel to be treated. Several imaging techniques have been proposed. Catheters incorporating mechanical rotation of ultrasonic transducers for imaging are disclosed in U.S. Pat. Nos. 4,794,931; 5,000,185; 5,049,130; and 5,024,234. These catheters scan in a plane normal to the catheter axis. Catheters employing phased array imaging systems are disclosed in U.S. Pat. Nos. 4,841,977 and 4,917,097. Catheters employing fiber optic imaging components are also known.

Generally deposits extend some longitudinal distance along the length of a vessel. To view different portions of the deposit a physician typically moves a handle attached to a proximal end of the imaging catheter along the vessel, for example, by pushing or pulling the catheter.

Imaging using computer-assisted reconstruction algorithms enables physicians to view a representation of the patient's interior intravascular structures in two or three dimensions (i.e., so-called three-dimensional or longitudinal view reconstruction). In this connection, image reconstruction algorithms typically employ data-averaging techniques which assume that the intravascular structure between an adjacent pair of data samples will simply be an average of each such data sample. Thus, the algorithms use graphical "fill in" techniques to depict a selected section of a patient's vascular system under investigation. Of course, if data samples are not sufficiently closely spaced, then lesions and/or other vessel abnormalities may in fact remain undetected (i.e., since they might lie between a pair of data samples and thereby be "masked" by the image reconstruction algorithms mentioned previously).

Even with the most skilled physician, it is practically impossible to manually exercise sufficiently slow constant rate longitudinal translation of the ultrasound imaging device (which thereby provides for a precisely known separation distance between adjacent data samples). In addition, with manual translation, the physician must manipulate the translation device while observing the conventional two-dimensional sectional images. This division of the physician's attention and difficulty in providing a sufficiently slow constant translation rate can result in some diagnostic information being missed. To minimize the risk that diagnostic information is missed, it is necessary to lengthen the imaging scan time which may be stressful to the patient. Similarly, it is difficult for physicians to manually control the translational rate of atherectomy catheters and other interventional devices that are longitudinally advanced and retracted through blood vessel and other body lumens.

U.S. Pat. No. 5,485,486 discloses an ultrasound imaging transducer which is capable of being translated longitudinally within a section of a patient's vascular system at a precise constant rate through the use of a longitudinal translation assembly. The longitudinal translation assembly moves the entire rotary drive assembly to provide the desired longitudinal movement of the transducer. Such an ability enables a series of precisely separated data samples to be obtained thereby minimizing (if not eliminating) distorted and/or inaccurate reconstructions of the ultrasonically scanned vessel section (i.e., since a greater number of more closely spaced data samples can reliably be obtained). Also, such an assembly can be operated in a "hands-off" manner which allows the physician to devote his or her attention entirely to the real-time images with the assurance that all sections of the vessel are displayed. While such a longitudinal translation assembly can work well, it is relatively large, bulky and heavy; it is expensive; and it is cumbersome to set up, in part because the rotary drive and longitudinal translation assemblies are wrapped in separate sterile drapes (plastic bags) for sterility.

SUMMARY OF THE INVENTION

The present invention is directed to a device for controlled longitudinal movement of an operative element, such as an ultrasound transducer, optical fiber rotary cutter, or the like within a catheter sheath of a catheter system. It is simple to set up and use, can be light in weight, is sufficiently simple in construction to be disposable if desired, and in the case of rotational operative elements, eliminates the bulk and weight of longitudinal translation assemblies designed to move entire rotary drive assemblies.

The device may be used as a part of a catheter system of the type including a case, a hollow sheath having proximal and distal ends, and a connecting member (such as a drive cable) housed within the sheath and having an operative element (such as an ultrasound transducer, optical fiber, or rotatable cutter) at its distal end. The case may comprise a handle, a catheter hub assembly, a motor drive unit for rotating a rotatable operative element as described in more detail below, or any other component which is able to be attached to a proximal end of the connecting member. A proximal end of the connecting member is coupled to the case to prevent relative longitudinal movement (although relative rotational movement will often be desired). A homeostasis valve, or other sheath-patient anchor, can be used to anchor an intermediate portion of the sheath to the patient at the point where the sheath enters the patient.

An operative element mover is connected near the proximal ends of the connecting member and the sheath and is used to longitudinally translate the operative element relative to the longitudinal axis of the sheath. The operative element mover includes a body, configured to be fixedly mountable to and dismountable from the case, and a sheath anchor movably mounted to the body for movement between first and second longitudinally spaced-apart positions relative to the body. The sheath anchor is securable to the sheath at a chosen position along the sheath. The operative element mover also includes a sheath anchor drive which moves the sheath anchor between the first and second positions so that the longitudinal distance between the chosen position on the sheath and the proximal end of the connecting member changes (i.e., increases or decreases). This movement causes the longitudinal position of the operative element within the sheath to change (i.e., move proximally or distally).

One of the primary advantages of the present invention results from the recognition that controlled longitudinal movement of the transducer, or other operative element within the sheath, can be achieved without moving the case to which the sheath and the drive cable, or other connecting member, are coupled. This permits the operative element mover of the present invention to be smaller and lighter weight than previous assemblies mounted directly to the case of a rotary drive assembly as described above.

According to one embodiment, both a case and an operative element mover can be contained within a single sterile drape (typically a plastic bag); therefore set up and use of the system is much less tedious compared with systems, such as three-dimensional imaging systems in which a rotary drive assembly and a linear transducer module are contained in separate sterile bags. With the present invention, the operative element mover is sufficiently simple and low cost that it may be supplied as a sterile, single-use component, so that only the rotary drive assembly need be placed in the sterile drape.

With the present invention only a portion of the sheath is moved; the sheath anchor drive can therefore be much less substantial than is required when a conventional longitudinal translator used to longitudinally translate an entire rotary drive assembly of a conventional ultrasound imaging system. This permits the sheath anchor drive to be powered by a relatively small battery so that the entire operative element mover can be self-contained requiring no separate power cords or mechanical drive lines.

An exemplary embodiment discloses the use of a rotatable ultrasound transducer as the operative element. Other imaging devices could be used as the operative element, such as phased array ultrasound transducers (such as those disclosed in U.S. Pat. Nos. 4,841,977 and 4,917,097), optical coherence tomography devices (as disclosed in U.S. Pat. No. 5,321,501), and other fiberoptic visualization devices. The operative element could also be a work-performing device, such as an atherectomy (see U.S. Pat. No. 4,794,931) or other cutter device, laser ablation devices (see U.S. Pat. No. 5,029,588), RF energy ablation devices, and other ablation energy delivery devices. The full disclosures of each of the aforementioned patents are incorporated herein by reference.

Other features and advantages of the invention will appear from the following description in which the preferred embodiment has been set forth in conjunction with the accompanying drawings.

BRIEF DESCRIPTION OF THE DRAWINGS

FIGS. 3A and 3B illustrate schematically the operation of the present invention;

FIGS. 7A and 7B show the assembly of FIG. 1 with the distal end of the sheath enlarged illustrating the bow in the sheath created when the anchor post is moved from the proximal position of FIG. 7A to the distal position of FIG. 7B.

DESCRIPTION OF THE EXEMPLARY EMBODIMENTS

Figure 1:
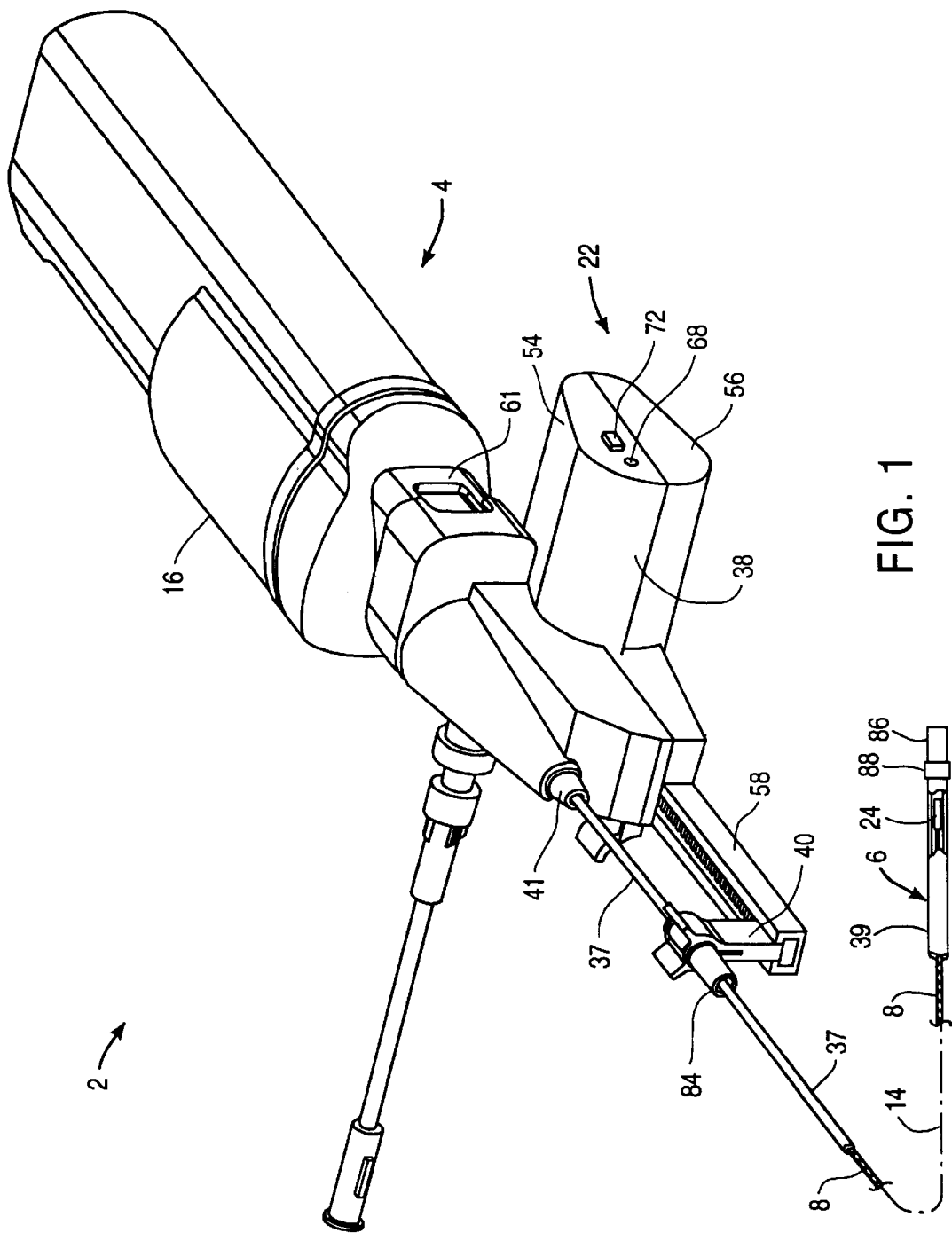
FIG. 1 is an isometric view of an operative element mover made according to the invention.

An exemplary embodiment of a catheter system made according to the invention comprises a rotary drive assembly 4 (FIG. 1) from which a flexible sheath 6 housing a connecting member such as drive cable 8 extends (FIG. 3A). Rotary drive assembly 4 can be conventional in construction, such as that shown in U.S. Pat. No. 5,485,846 or that sold by Boston Scientific Corporation of Natick, Mass. as Automatic Catheter Pullback Device, catalog no. A7015, and Motor Drive Unit, catalog no. 15018. Except as discussed below, the particular construction of rotary drive assembly 4 is not a part of this invention and will not be discussed in detail.

Rotary drive assembly 4 includes a rotary driver 10, see FIG. 3A, which is coupled to the proximal end 12 of drive cable 8 and causes drive cable 8 to rotate about the longitudinal axis 14 of sheath 6, rotary driver 10 being housed within a case 16. Rotary driver 10 is coupled to a power source, not shown, external of case 16. A proximal end 18 of sheath 6 is also housed within case 16 and passes through an opening 20 formed in case 16. Before describing the construction of operative element mover 22, which is mountable to and dismountable from case 16, a conventional way of providing longitudinal movement for the transducer 24 at the distal end 26 of drive cable 8 will be discussed with reference to FIGS. 2A and 2B.

Figure 2A:
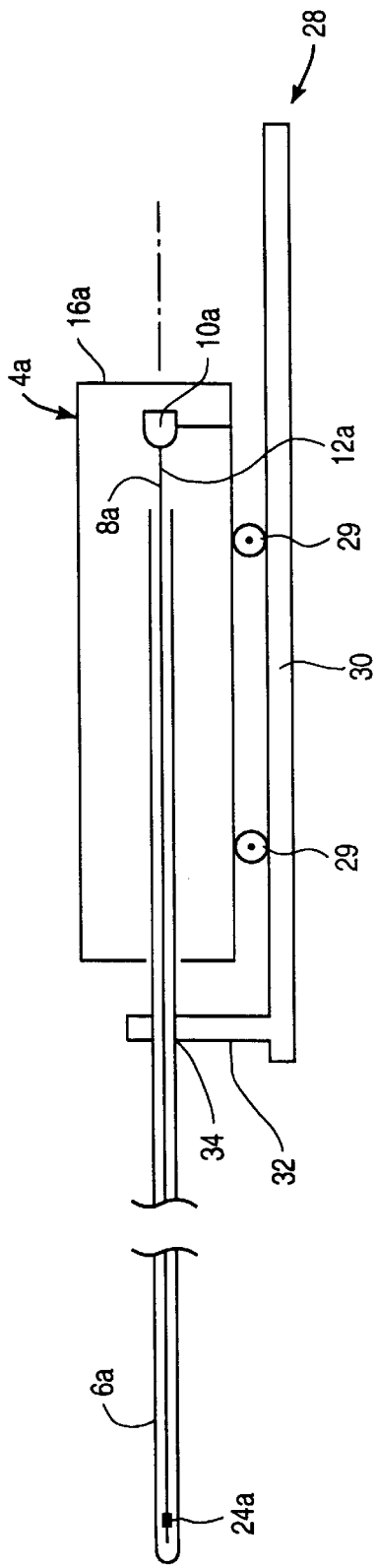
FIGS. 2A and 2B are schematic cross-sectional side views of a conventional ultrasound imaging system.
Figure 2B:
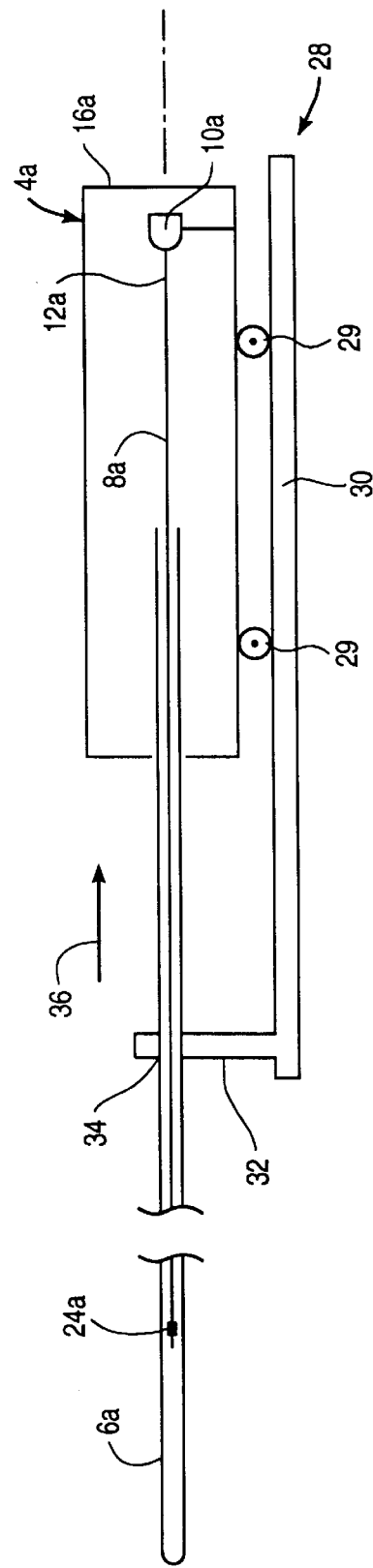

FIG. 2A illustrates a conventional rotary drive assembly 4a having a case 16a housing a rotary driver 10a. Rotary driver 10a is coupled to and drives the proximal end 12a of drive cable 8a to rotate transducer 24a to obtain the desired image. Appropriate conventional signal lines are typically carried along drive cable 8a, are coupled to transducer 24a and will not be shown or described. To generate the desired three-dimensional image, rotary drive assembly 4a is mounted to a longitudinal drive assembly 28. Drive assembly 28 includes a longitudinal driver 29 constructed to cause the entire rotary drive assembly to move longitudinally on the base 30 of drive assembly 28 as shown in FIGS. 2A and 2B. Longitudinal drive assembly 28 also includes an anchor post 32 which is secured to a chosen position 34 along sheath 6a. Therefore, when rotary drive assembly 4a is moved longitudinally in the direction of arrow 36, shown in FIG. 2B, sheath 6a is maintained in position while drive cable 8a is pulled longitudinally through sheath 6a to reposition transducer 24a. As discussed above, some of the problems with using this type of arrangement is that longitudinal drive assembly 28 can be relatively large, heavy, cumbersome to use and expensive to purchase.

Figure 6:
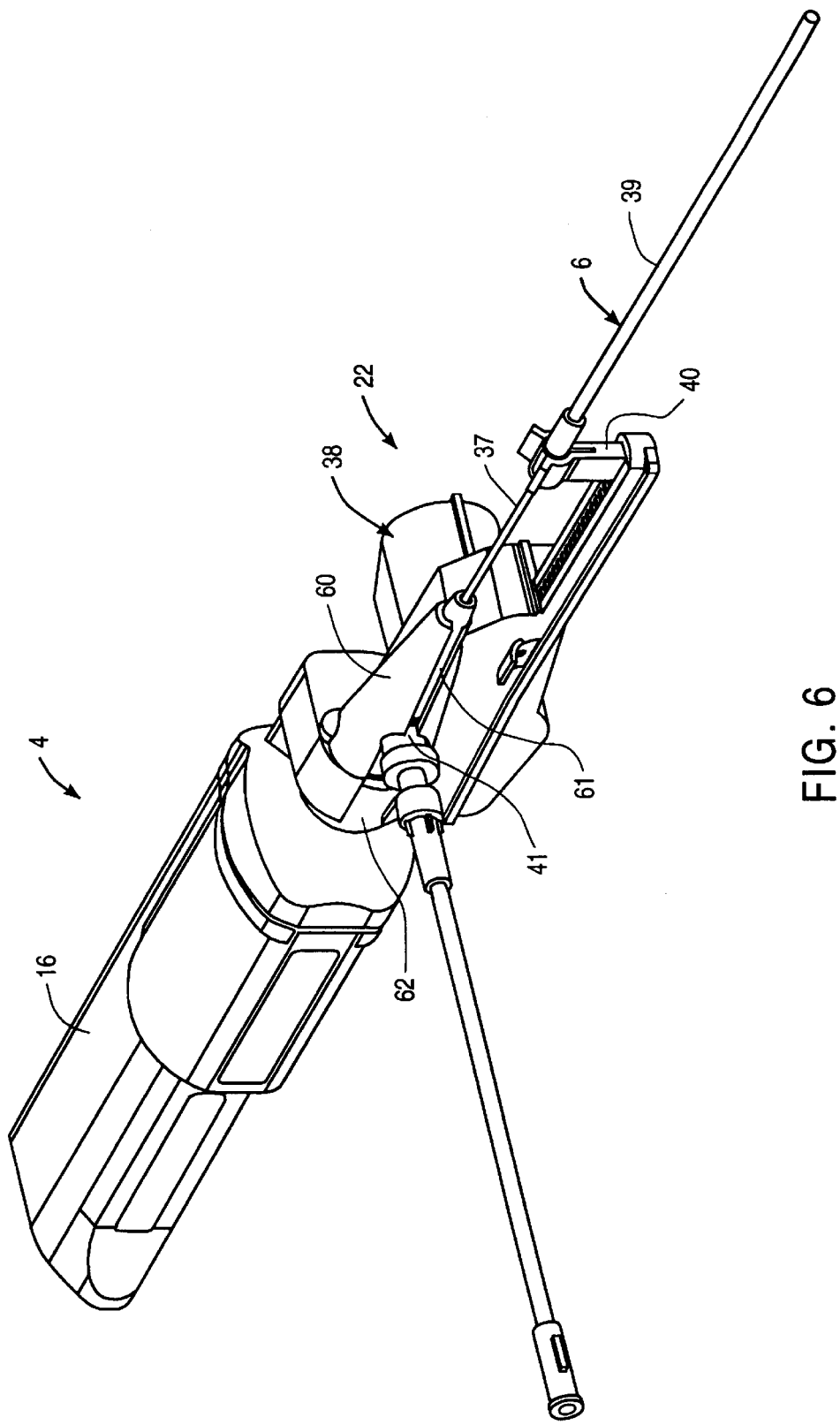
FIG. 6 is an isometric view of the operative element mover of FIGS. 1 and 4 taken from the opposite side to show the opening in the body of the operative element mover.
Figure 6A:
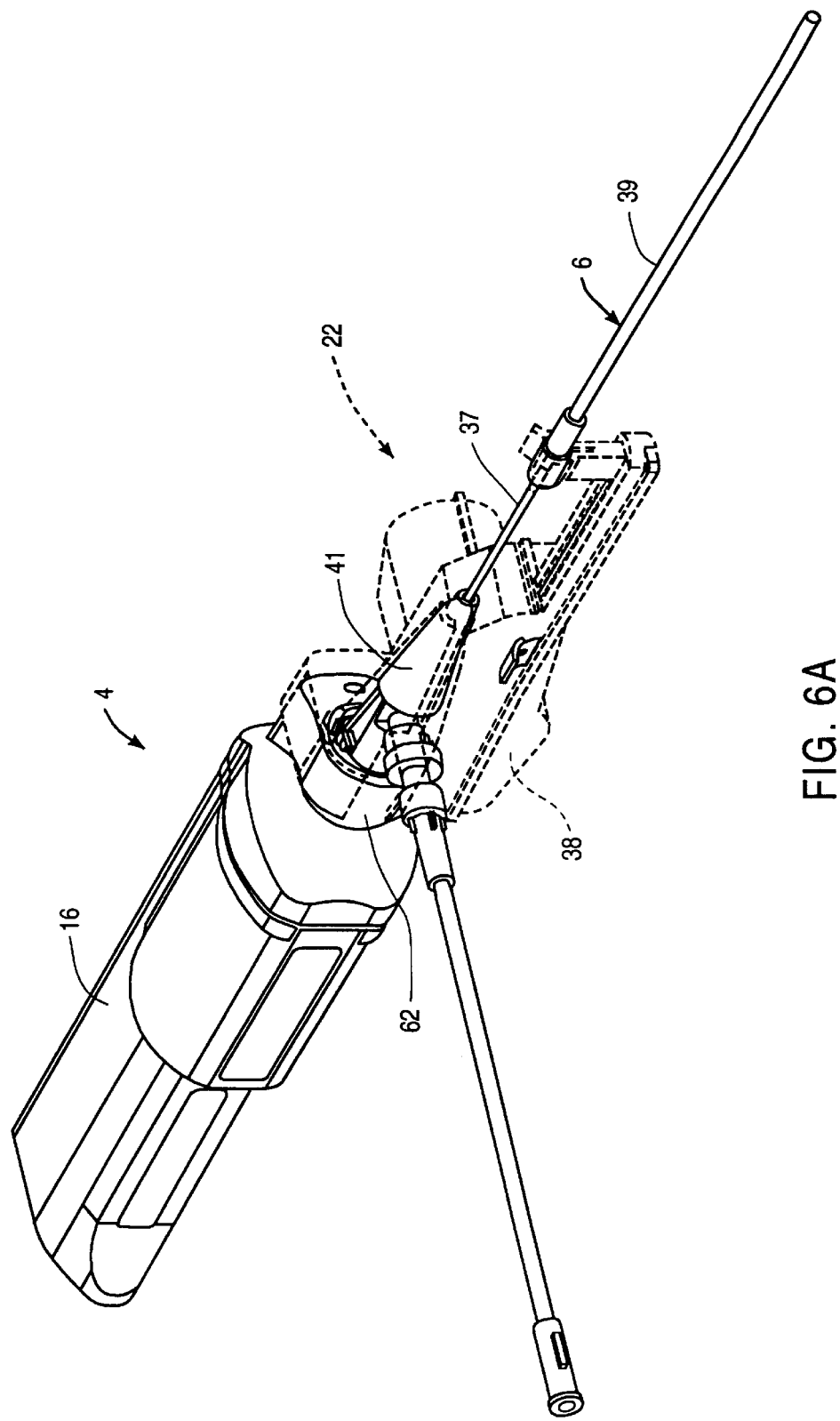
FIG. 6A is a view similar to FIG. 6 but with the operative element mover shown in dashed lines.

The present invention will now be discussed with reference to FIGS. 3A and 3B showing operative element mover 22 in schematic form. Sheath 6 includes a reduced diameter, telescoping portion 37 which fits within a main sheath portion 39 at one end and extends from a proximal end adapter 41 (FIG. 6A) at the other. Such catheter constructions are described generally in U.S. Pat. No. 5,314,408, the full disclosure of which is incorporated herein by reference (see FIGS. 11A and 11B in particular). Transducer mover 22 includes a body 38 detachably mounted at a fixed position on case 16 and an anchor post 40 extending from a drive rack 42 which slides along a support surface 44 formed by body 38. Anchor post 40 is, in the disclosed embodiment, configured to be clipped to main sheath portion 39 at a proximal end 45 of sheath portion 39. Transducer mover 22 also includes a sheath anchor drive 46 which engages drive rack 42 and causes anchor post 40 to move in the direction of arrow 48 of FIG. 3B. Doing so causes the proximal end 45 of main sheath portion 39 to move distally away from proximal end 12 of drive cable 8 and proximal end 18 of telescope sheath portion 37 (which are longitudinally fixed within the case 16 which is immobile relative to the base 38). As a result of the distal movement of the main sheath portion 39, the telescoping portion 37 is further exposed as shown in FIG. 3B. Such distal extension of the sheath portion 39 causes the distance between the fixed proximal end of drive cable 8 and homeostasis valve 50 to increase by the length of movement of anchor post 40 in a distal direction (arrow 48). Transducer 24 therefore moves a like distance in a proximal direction (arrow 52) from the position of FIG. 3A to the position of FIG. 3B. By comparing the prior art embodiment of FIGS. 2A and 2B to the embodiment of FIGS. 3A and 3B, it can be appreciated that transducer mover 22 can be much less substantial in structure, since it only needs to move sheath 6, than the longitudinal drive assembly of FIGS. 2A and 2B, which needs to move the entire rotary drive assembly 4a.

FIGS. 1, 4, 5, 6 and 6A illustrate a specific construction of transducer mover 22. Body 38 (FIG. 6) of transducer mover 22 has a top 54 (FIG. 4) which overlies and is mountable to a bottom 56 of the body. Top 54 and bottom 56 are secured to one another typically using adhesives or thermal welding techniques. Bottom 56 has an extension 58 which defines support surface 44, see FIG. 5, on which drive rack 42 is slidably supported. Top 54 includes a molded nose assembly 60 having an elongate gap or slot 61; assembly 60 is sized and configured to snap onto and be secured to the distal or nose portion 62 of case 16 and over proximal end adapter 41 of the ultrasound imaging system 2 (best seen in FIG. 6A). Therefore, the configuration of nose assembly 60 will depend largely upon the configuration of nose portion 62 of case 16 and proximal end adapter 41.

Figure 4:
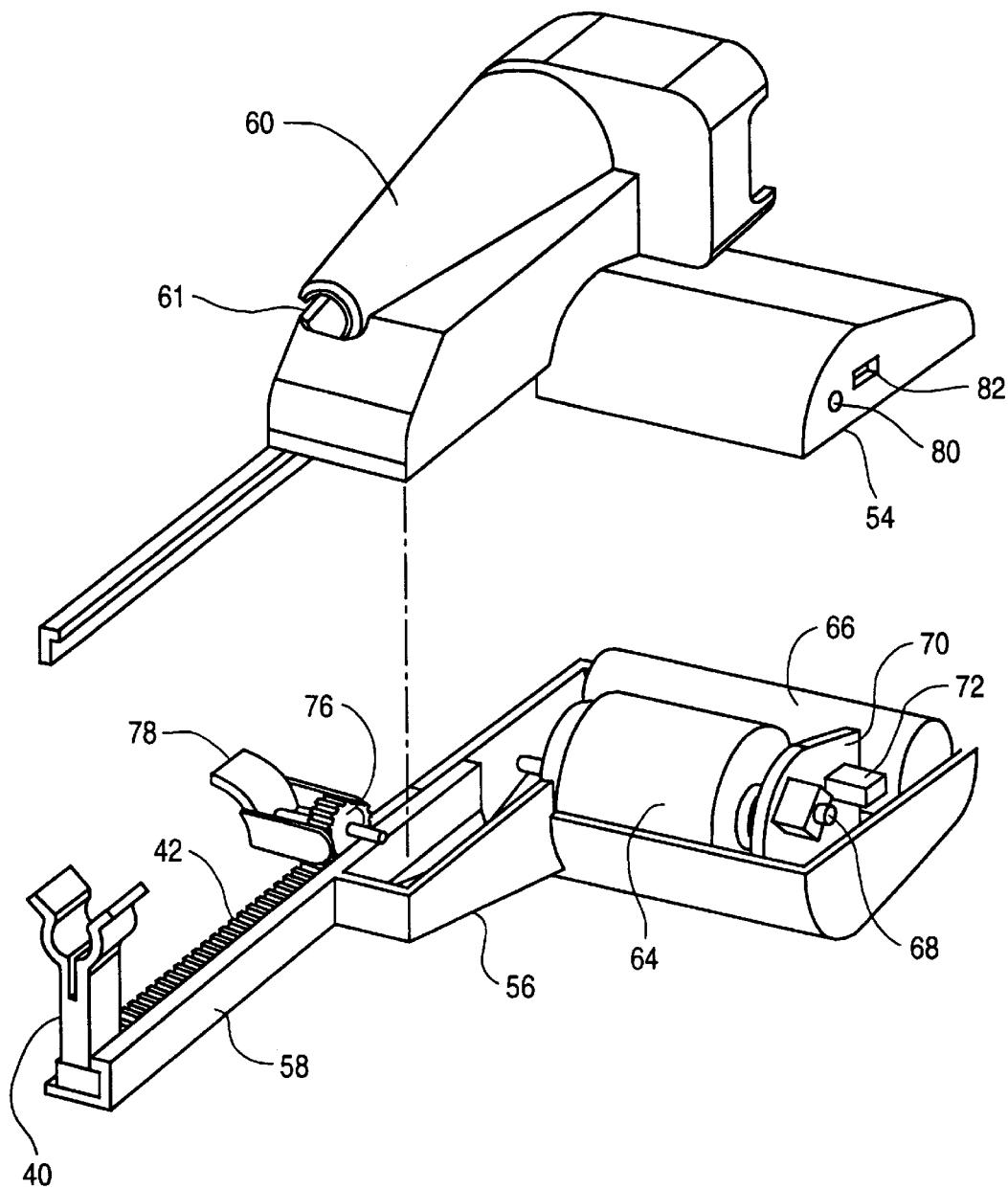
FIG. 4 is a partially exploded isometric view of the operative element mover of FIG. 1 showing the top of the mover body spaced apart from the remainder of the mover.
Figure 5:
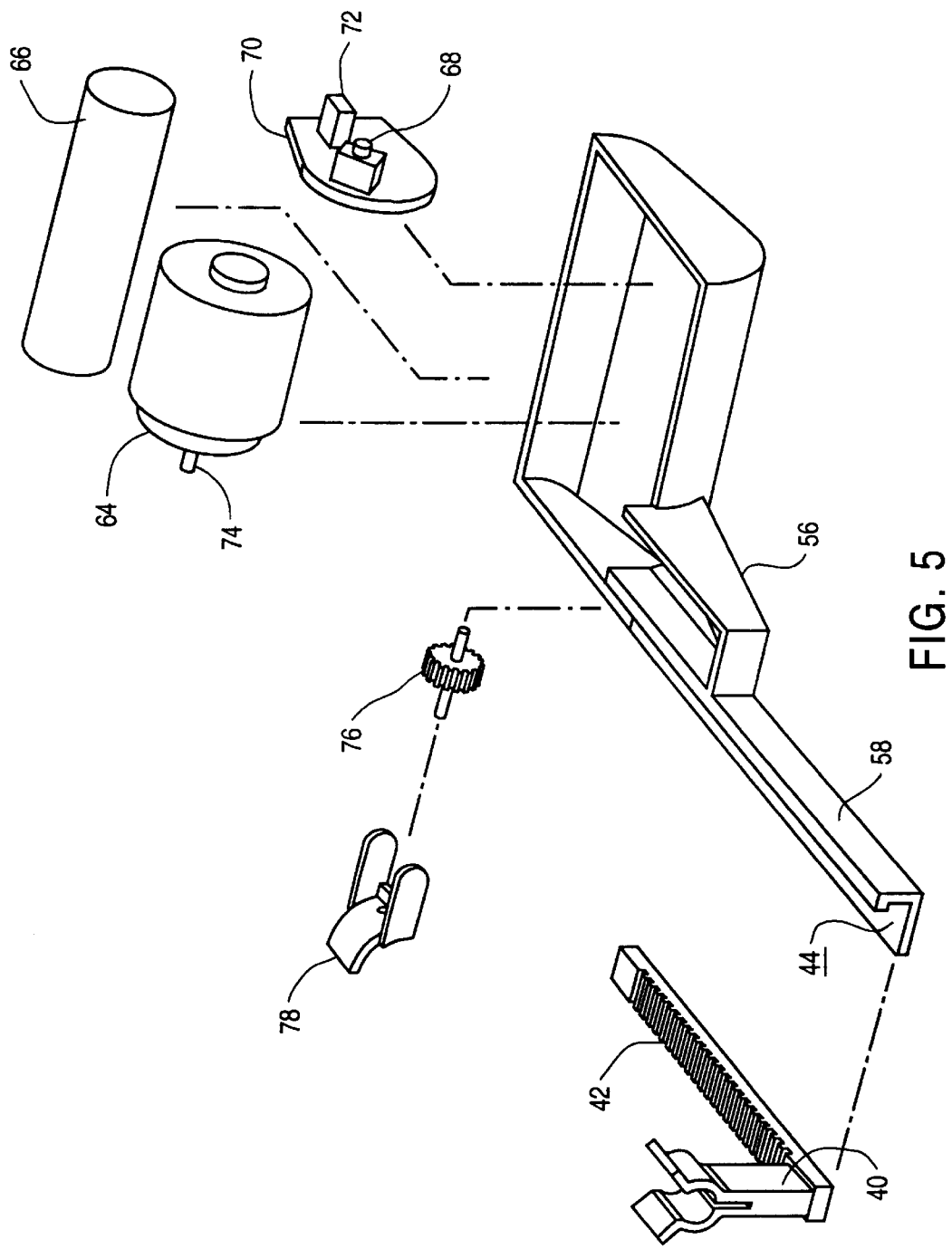
FIG. 5 is an exploded isometric view of the operative element mover of FIG. 4 with the exception of the case top.

Sheath anchor drive 46, illustrated schematically in FIGS. 3A and 3B, includes a number of components illustrated in FIGS. 4 and 5. Specifically, drive 46 includes a DC motor 64 powered by a battery 66 through a switch 68. Switch 68 is mounted to a printed circuit board 70. An LED 72 is also mounted to printed circuit board 70, the LED being illuminated when motor 64 is running. Motor 64 has a drive shaft 74 which is coupled to a drive gear 76 by a suitable drive train, not shown. The drive train could be a set of gears, a belt drive, or other suitable drive means. Drive gear 76 is retained against drive rack 42 by a clutch 78. Clutch 78 helps to ensure that motor 64 does not drive drive cable 8 with force sufficient to injure the patient or damage the system components. Top 54 has a pair of openings 80, 82 aligned with switch 68 and LED 72. Switch 68 and LED 72 are positioned so that switch 68 and LED 72 each pass a short distance through openings 80, 82. In some situations it may be desirable to restrict access to switch 68; one way to do so is by sizing switch 68 so it is accessible through opening 80 but does not extend through the opening. This alternative design would help to prevent inadvertent actuation of drive 46 since switch 68 could be depressed only with the use of an instrument or tool, such as the end of a ballpoint pen.

In use the physician guides the distal end 86 (FIGS. 1, 3A and 3B) of sheath 6, typically using a guidewire (not shown), together with drive cable 8, to the desired position within the patient, typically using conventional fluoroscopic techniques. One or both of distal ends 26, 86 typically include radiopaque markers for this purpose. FIGS. 1, 7A and 7B show a radiopaque band 88 at distal end 86 of sheath 6. Once in position, proximal end 12 of drive cable 8 is coupled to rotary driver 10 and proximal end 18 of sheath 6 is positioned within case 16. Case 16 is then secured about those proximal ends and the physician can conduct the desired ultrasound scan of the patient's vessel by rotating drive cable 8 in a pure rotational or an oscillating manner, as is conventional. If it is desired to create an ultrasound scan while transducer 24 is pulled longitudinally along longitudinal axis 14 of sheath 6, transducer mover 22 is mounted to nose portion 62 of case 16 in a snap-fit type of arrangement. When this is accomplished anchor post 40 is clipped to an anchor housing 84, housing 84 being fixed to proximal end 45 of main portion 39 of sheath 6. See FIGS. 3A and 7A. The use of housing 84 helps keep sheath 6 from being collapsed by anchor post 40 or kinked during use. With rotary drive 10 rotating drive cable 8, switch 68 is depressed thus actuating motor 64 to cause drive gear 76 to rotate slowly causing drive rack 42 to move in the direction of arrow 48 thus pushing proximal end 45 of main sheath portion 39 in the distal direction over telescoping sheath portion 37. Thus, the distance between the sheath anchor post 40 and the homeostasis valve 50 is decreased and the sheath 6 is deflected or "bowed" as illustrated in FIG. 7B. Such lateral deflection of the sheath 6 draws the connecting member (drive cable) 8 proximally out from that portion of the sheath anchored within the patient's vasculature by the homeostasis valve 50, thus translating transducer 24 in the direction of arrow 52 (FIG. 3B). Appropriate ultrasound data can be collected as transducer 24 is moved in both rotary and longitudinal directions. Movement of main sheath portion 39 can be halted by depressing switch 68 or by disengaging anchor post 40 from anchor housing 84. Once the transducer 24 has been drawn proximally, as shown in FIG. 7B, the transducer mover 22 can be used to advance the transducer distally by translating the anchor post 40 in the proximal direction relative to the body at the transducer mover 22.

To ensure sterility of the procedure, a sterile drape (typically a plastic bag) is placed over rotary drive assembly 4 and transducer mover 22 with sheath 6 extending through an opening formed in the sterile drape distal of anchor post adapter 84. Unlike the prior art in which separate sterile drapes need to be used for each of the rotary drive assembly and the longitudinal drive assembly, only a single sterile drape needs to be used with the present invention. If transducer mover 22 is supplied as a sterile assembly intended for one-time use, rotary drive assembly 4 is covered by the sterile drape and the transducer mover is mounted over the encased assembly 4. The transducer mover 22 may then be discarded after use. The rotary drive assembly 4 may be reused. At times rotary drive assembly 4 may be in use when it is decided to use a reusable transducer mover 22; in such event transducer mover 22 would be covered by a sterile drape and then mounted to assembly 4.

The disclosure of each patent referred to above is incorporated by reference.

Modification and variation can be made to the disclosed embodiment without departing from the subject invention as defined in the following claims. For example, drivers other than drive gear 76 and drive rack 42, such as a worm and worm gear drive, a friction belt drive or a toothed belt drive, could be used. Sheath 6 could be increased in length by other methods, such as by deflecting sheath 6 laterally to create a bow or curve in the sheath. Instead of using a telescoping sheath 6, proximal end 18 of sheath could be slidably housed within proximal end adapter 41 so that extension of anchor post would cause sheath 6 to extend from adapter 41, also in a telescoping manner. Instead of using battery 66, an external source of power, such as the power source used with rotary drive assembly 4 or a separate external power source, could be used. Transducer mover 22 could be mountable to case 16 of rotary drive assembly 4 using threaded fasteners, clips, or other means. Sheath 6 is preferably anchored by homeostasis valve 50; however other structure for anchoring a position along the sheath relative to the patient, such as by the use of a clamp extending from the operating table, could be used. Body 38 could be reconfigured so that extension 58 is eliminated; drive rack 42 would then be supported in a cantilevered manner by structure located beneath nose assembly 60.

Figure 8:
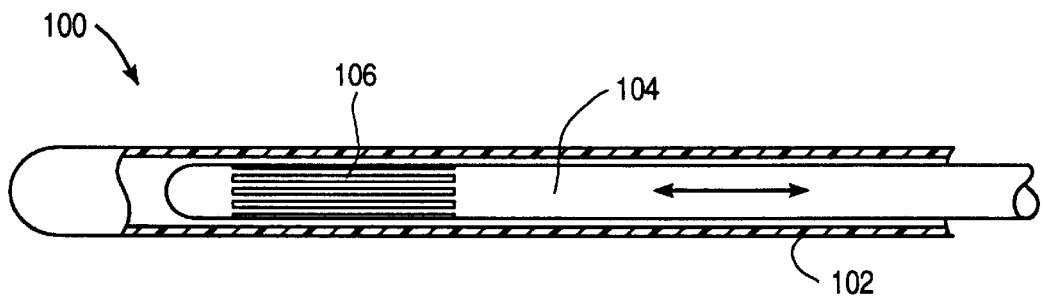
FIG. 8 illustrates a phased array ultrasonic imaging catheter that may be part of the catheter system of the present invention.

A variety of other specific catheter constructions can be substituted for the ultrasonic imaging catheter described above. Indeed, the operative element mover of the present invention is useful with virtually any catheter having an outer sheath and an inner element that requires axial translation within the sheath. Specific examples of such other catheters include phased array ultrasonic imaging catheters 100, as shown in FIG. 8. The phased array catheter has an outer sheath 102 and an inner connecting member 104 which carries an operative element comprising a plurality of discrete ultrasonic transducer elements 106 near its distal end. The construction of such catheters is well known and described in a number of patents including U.S. Pat. No. 4,841,977, previously incorporated herein by reference. The catheter 100 may be connected to the operative element mover 22 by securing a proximal end of the sheath 102 to the anchor post 40 and a proximal end of the connecting member 104 to body 38 (or other handle component). Usually, the connecting member 104 will not be rotated.

Figure 9:
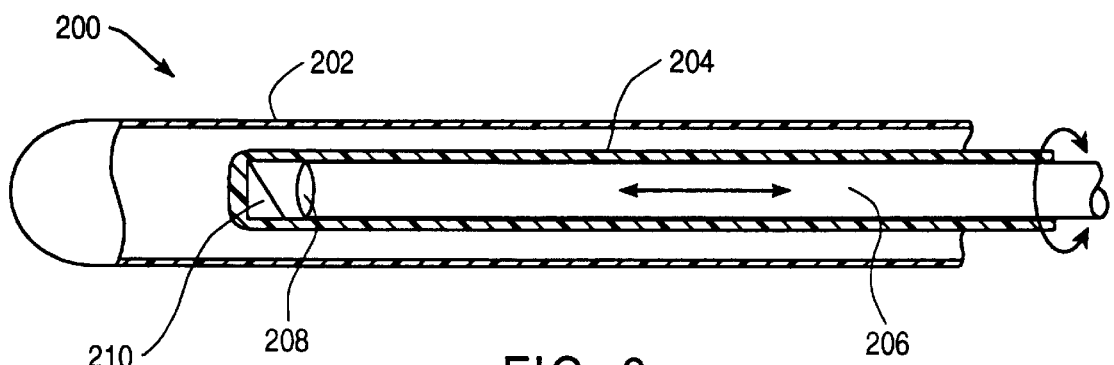
FIG. 9 illustrates an optical coherence tomography catheter that may be part of the catheter system of the present invention.

The operative element mover 22 may also be used with optical coherence tomography (OCT) catheters 200, as illustrated in FIG. 9. Catheter 200 also includes a sheath 202 and a connecting member 204. The connecting member 204 carriers one or more optical fibers, a lens 208, and a mirror 210 having a surface disposed at 45° relative to the longitudinal direction. Intravascular OCT imaging relies on rotation of the mirror 210 to scan a light beam from and to the optical fiber 206, as described in more detail in U.S. Pat. No. 5,321,501, previously incorporated herein by reference. Incorporation of the catheter 200 into the systems of the present invention is very similar to that described in connection with system 2. A case (not shown) including a motor driver for rotating the connecting member 204 is mounted in the operative element mover 22. The sheath 202 is connected to the anchor post 40 and a proximal end of the connecting member 204 held proximally in place in the motor drive.

Figure 10:
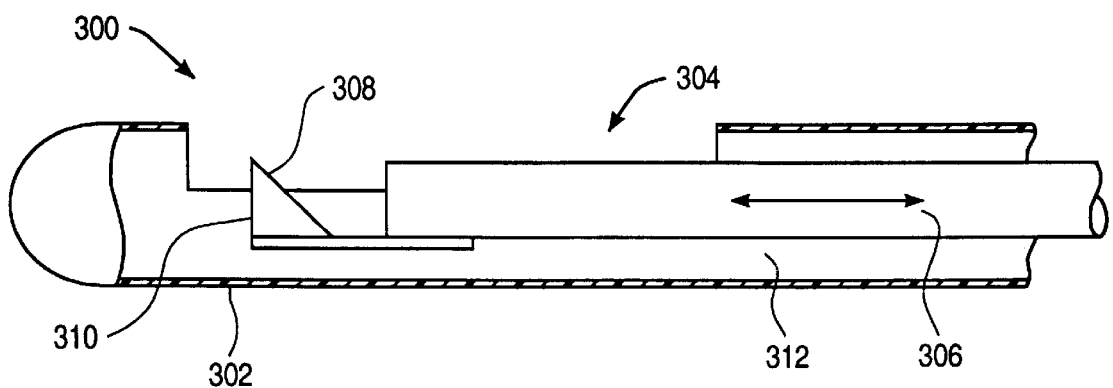
FIG. 10. illustrates a laser ablation catheter that may be part of the catheter system of the present invention.

A laser catheter 300 is illustrated in FIG. 10. The catheter 300 includes a sheath 302 having a longitudinal aperture 304. An optical fiber 306 capable of directing a laser beam against a 45° reflective surface 308 of mirror 310 is axially translatably mounted within lumen 312 of the sheath 302. The sheath 302 may be secured to the operative element driver 22 in a manner which is analogous to the phased array ultrasonic catheter 100 of FIG. 8. No rotation of the optical fiber 306 will be required.

Figure 11:
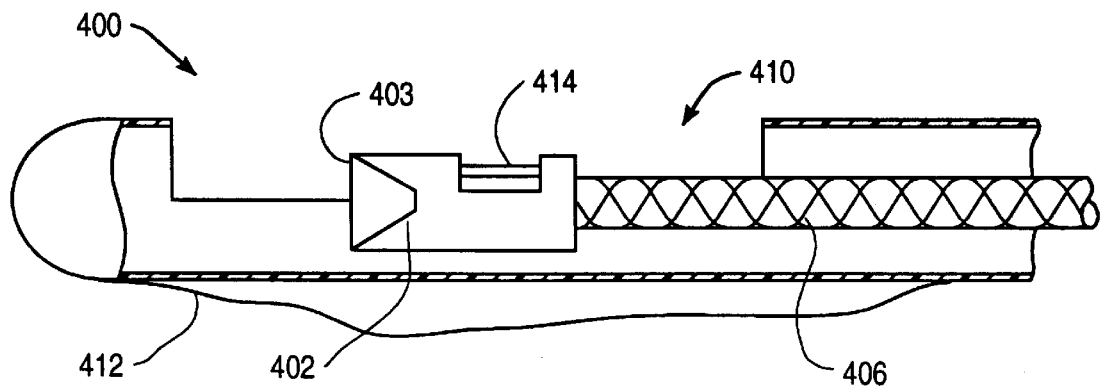
FIG. 11 illustrates an atherectomy catheter that may be part of the catheter system of the present invention.

The operative element mover 22 may also be used with mechanical interventional catheters, such as atherectomy catheter 400 illustrated in FIG. 11. the atherectomy catheter is similar to that shown in FIG. 8 of U.S. Pat. No. 4,794,931, previously incorporated herein by reference. The catheter 400 comprises a rotatable cutter 402 connected to a distal end of rotatable drive cable (connecting member) 406. The cutter 402 may be axially translated and rotated by the cable 406 so that a circular cutting edge 408 of the cutter 402 can cut atheroma urged into aperture 410 by inflation of balloon 412. Optionally, an ultrasonic transducer 414 may be mounted on the cutter 402 to provide imaging as well as atheroma removal. Connection of the catheter 400 to the operative element mover 22 will be entirely analogous to that described above for catheter system 2.

What is claimed is:

1. A catheter system comprising:
   a case;
   a catheter assembly, extending from the case, comprising a hollow sheath and a connecting member at least partially housed within the sheath;
   the sheath having proximal and distal ends and defining a longitudinal axis;
   an operative element;
   the connecting member having the operative element secured thereto and a proximal end coupled to the case;
   an operative element mover comprising:
      a body fixedly mountable to and dismountable from the case;
      a sheath anchor movably mounted to the body for movement between first and second positions relative to the body;
      the sheath anchor comprising a portion securable to the sheath at a chosen position; and
      a sheath anchor drive, carried by the body, operably coupled to the sheath anchor so to move the sheath anchor, and the chosen position of the sheath therewith, between the first and second positions so a longitudinal distance between the chosen position along the sheath and the proximal end of the connecting member changes to cause the longitudinal position of the operative member within the sheath to change.

2. The system according to claim 1 wherein the operative element is selected from the group consisting of ultrasound transducers, optical fibers, and rotary cutters.

3. The system according to claim 1 further comprising a sheath-patient anchor for anchoring the sheath to the patient where the sheath enters the patient.

4. The system according to claim 3 wherein the sheath-patient anchor comprises a hemostasis valve.

5. The system according to claim 1 wherein the body comprises a nose assembly for clip-mounting the body to the case.

6. The system according to claim 1 wherein the sheath anchor drive comprises a motor connected to a battery through a user-activated switch, the motor and battery housed within the body.

7. An operative element mover for a catheter having a sheath and a connecting member longitudinally movable relative to the sheath, the operative element mover comprising:
   a body;
   a sheath anchor comprising a portion securable to the sheath at a chosen position; and
   a sheath anchor drive, carried by the body, operably coupled to the sheath anchor so to longitudinally move the sheath anchor and the chosen position of the sheath therewith between the first and second positions, so a longitudinal distance between the chosen position along the sheath and the proximal end of the connecting member changes to cause the longitudinal position of the operative element within the sheath to change.

8. An operative element mover as in claim 7 wherein the body is removably securable to a case attached to a proximal end of the connecting member.

9. An improved catheter system of the type including a case, a hollow sheath defining a longitudinal axis, a connecting member at least partially housed within the sheath and having a proximal end coupled to the case, an operative element secured to the connecting member, the improvement comprising:
   an operative element mover comprising:
      a body fixedly mountable to and dismountable from the case; and
      a longitudinally movable anchor post carried by the body and attachable to the sheath at a chosen position for changing the longitudinal distance between a proximal position on the sheath and the proximal end of the connecting member so to change the longitudinal position of the operative element within the sheath in an opposite direction.

10. A catheter system comprising:
   a case;
   a rotary driver housed within the case;
   a hollow sheath having proximal and distal ends and defining a longitudinal axis;
   an operative element;
   a drive cable at least partially housed within the sheath and having the operative element secured thereto and a proximal end coupled to the rotary driver, so that operating the rotary driver rotates the drive cable and the operative element therewith within the sheath and about the longitudinal axis;
   an operative element mover comprising:
      a body fixedly mountable to and dismountable from the case;
      a sheath anchor movably mounted to the body for movement between first and second positions relative to the body;
      the sheath anchor comprising a portion securable to the sheath at a chosen position; and
      a sheath anchor drive, carried by the body, operably coupled to the sheath anchor so to move the sheath anchor, and the chosen position of the sheath therewith, between the first and second positions so the longitudinal distance between the chosen position along the sheath and the proximal end of the drive cable changes to cause the longitudinal position of the operative element within the sheath to change in the opposite direction.

11. A catheter system as in claim 10 wherein the operative element is selected from the group consisting of ultrasound transducers, optical fibers, and rotary cutters.

12. An operative element mover for use with a catheter system of the type including a case, a hollow sheath defining a longitudinal axis, an operative element, a connecting member at least partially housed within the sheath and having the operative element secured thereto and a proximal end coupled to the case, said operative element mover comprising:
   a body comprising a case-mountable/dismountable portion; and
   a positioner, carried by the body and secured to a chosen position of said sheath, which translates a proximal portion of the sheath relative to the proximal end of the connecting member so to change the longitudinal distance between the chosen position along the sheath and the proximal end of the connecting member which changes the position of the operative element within the sheath.

13. A method for longitudinally moving an operative element carried by a connecting member within a hollow sheath of a catheter system comprising the following steps:
   mounting a body of an operative element mover to a fixed location on a case of the catheter system;
   securing a sheath anchor to a chosen position along the sheath extending from an exit point on the case;
   moving the sheath anchor from a first position to a second position causing the longitudinal distance between the chosen position and the exit point on the case to change; and
   preventing a change in a longitudinal distance between a location at which the sheath enters a patient's body and the chosen position along the sheath during said moving step, whereby the longitudinal position of the operative element within the sheath changes during the sheath moving step.

14. The method according to claim 13 wherein the moving step includes the step of moving said proximal portion of the sheath away from the case to proximally retract the operative element within the sheath.

15. The method according to claim 13 wherein said mounting step is carried out by clipping said body to said case.

16. The method according to claim 13 further comprising the step of encompassing said body and said case within a sterile drape.

17. The method according to claim 16 wherein said encompassing step is carried out using a single plastic bag.

18. The method according to claim 13 further comprising the steps of encompassing said body within a sterile drape prior to said mounting step.

19. A method for longitudinally translating a distal end of a connecting member having an operative element secured thereon, disposed in a hollow sheath, said method comprising:
   longitudinally fixing a proximal end of the connecting member;
   longitudinally fixing a distal section of the sheath, wherein the distal end of the connecting member lies within said fixed distal section;

longitudinally translating the proximal end of the sheath relative the fixed proximal end of the connecting member, whereby a portion of the sheath proximal to the fixed distal section is laterally deflected to cause relative movement of the connecting member which changes the position of the operative element within the sheath.

20. A method as in claim 19 wherein the proximal end of the sheath is advanced distally relative to the fixed proximal end of the connecting member to draw the connecting member and the operative element proximally within the fixed distal section of the sheath.

21. A method as in claim 19 wherein the proximal end of the sheath is drawn proximally relative to the fixed proximal end of the connecting member to advance the connecting member and the operative element distally within the fixed distal section of the sheath.

\* \* \* \* \*